United States Patent [19]

Volkamer et al.

[11] 4,310,388

[45] Jan. 12, 1982

[54] ISOLATION OF A CONJUGATED DIOLEFIN FROM A $C_4$- OR $C_5$ HYDROCARBON

[75] Inventors: Klaus Volkamer, Frankenthal; Klaus Broellos, Seeheim; Alfred Lindner, Bobenheim-Roxheim; Ulrich Wagner, Limburgerhof; Hans-Martin Weitz, Bad Duerkheim; Klaus-Jüergen Schneider, Neustadt, all of Fed. Rep. of Germany

[73] Assignee: BASF Aktiengesellschaft, Fed. Rep. of Germany

[21] Appl. No.: 126,898

[22] Filed: Mar. 3, 1980

[30] Foreign Application Priority Data

Mar. 23, 1979 [DE] Fed. Rep. of Germany ....... 2911395

[51] Int. Cl.$^3$ ............................ B01D 3/40; C07C 7/08
[52] U.S. Cl. ........................................ 203/51; 203/53; 203/58; 203/60; 585/864; 585/865
[58] Field of Search ....................... 203/51, 54, 55, 56, 203/53, 60, 58, 63, 62; 585/864–866; 588/810

[56] References Cited

U.S. PATENT DOCUMENTS

| | | | |
|---|---|---|---|
| 2,366,360 | 1/1945 | Semon | 203/56 |
| 2,455,803 | 12/1948 | Pierotti | 203/51 |
| 2,993,841 | 7/1961 | Sarno | 203/51 |
| 3,242,227 | 3/1966 | Kroeper et al. | |
| 3,436,438 | 4/1969 | Takao et al. | |
| 3,681,202 | 8/1972 | Funkhauser | 203/60 |
| 3,707,575 | 12/1972 | Muller et al. | 203/60 |
| 3,851,010 | 11/1974 | Rescalli et al. | 203/51 |
| 4,038,156 | 7/1977 | Knott et al. | 203/60 |
| 4,081,332 | 3/1978 | Hein | 203/56 |

FOREIGN PATENT DOCUMENTS

2738418 3/1978 Fed. Rep. of Germany ........ 203/51

OTHER PUBLICATIONS

The Soviet Chemical Industry, No. 11, 11/71, pp. 719–723.

*Primary Examiner*—Wilbur L. Bascomb, Jr.
*Attorney, Agent, or Firm*—Keil & Witherspoon

[57] ABSTRACT

A process for isolating a conjugated diolefin from a $C_4$- or $C_5$-hydrocarbon mixture containing the diolefin, by single-stage or multi-stage extractive distillation using a selective solvent, wherein the selective solvent is a solvent mixture which comprises
(a) from 50 to 99 percent by weight of a selective solvent boiling at from 140° C. to 260° C. and
(b) from 1 to 50 percent by weight of an organic solvent boiling at from 45° C. to 125° C.

2 Claims, No Drawings

ISOLATION OF A CONJUGATED DIOLEFIN FROM A C$_4$- OR C$_5$ HYDROCARBON

The present invention relates to a process for isolating a conjugated diolefin from a C$_4$- or C$_5$-hydrocarbon mixture by extractive distillation with the aid of a selective solvent.

Extractive distillation is a known process for separating mixtures which are not easily separable by conventional fractional distillation, for example if the components to be separated form an azeotrope or if the differences in the relative volatilities are slight. In extractive distillation, a solvent of relatively low volatility is introduced into the distillation column in such amounts that the differences in the relative volatilities of the components to be separated are increased and hence distillative separation becomes possible. Typical examples of the application of extractive distillation are to be found, for instance, in C. S. Robinson et al. "Elements of Fractional Distillation", 4th edition, McGraw-Hill Company, Inc., New York, (1959), page 291.

It is known, for example from German Laid-Open Application DOS No. 2,742,148, German Published Application DAS No. 1,568,902. German Pat. No. 1,163,795 or The Soviet Chemical Industry, No. 11, November 1971, pages 719–723, that conjugated diolefins can be isolated from a C$_4$- or C$_5$-hydrocarbon mixture by extractive distillation using a selective solvent. The selective solvents can be used anhydrous. However, in this method, which is used especially in the case of solvents sensitive to hydrolysis, the C$_4$- or C$_5$-hydrocarbon selectivity is in general insufficient. Hence, water has been added to the selective solvents to increase the selectivity and to lower the boiling point. However, such addition of water to the selective solvent has the disadvantage that it reduces the solubility of the C$_4$- or C$_5$-hydrocarbons in the selective solvent, so that the amount of selective solvent circulating in the extraction unit is correspondingly increased. Furthermore, the addition of water can have an adverse effect on the viscosity and hence on the tray efficiency of the selective solvent.

It is an object of the present invention to provide a process for isolating a conjugated diolefin from a C$_4$- or C$_5$-hydrocarbon mixture containing the diolefin, by single-stage or multi-stage extractive distillation using a selective solvent, wherein the amount of selective solvent circulating in the extraction unit can be kept low.

According to the invention, this object and other objects and advantages are achieved by a process for isolating a conjugated diolefin from a C$_4$- or C$_5$-hydrocarbon mixture containing the diolefin, by single-stage or multi-stage extractive distillation using a selective solvent, wherein the selective solvent used is a solvent mixture which comprises
  (a) from 50 to 99 percent by weight of a selective solvent boiling at from 140° C. to 260° C. and
  (b) from 1 to 50 percent by weight of an organic solvent boiling at from 45° C. to 125° C.

The solubility of the C$_4$- or C$_5$-hydrocarbons in the solvent mixture which according to the invention is to be used as the selective solvent is substantially increased compared to the conventional processes, whilst the C$_4$- or C$_5$-hydrocarbon selectivity is similar, so that the amount of selective solvent circulating in the extraction unit for isolating the conjugated diolefin can be greatly reduced. This in particular results in a great reduction in the investment required for the extraction unit, and in the consumption of steam and electrical energy. Furthermore, the solvent mixture to be used according to the invention has a lower viscosity, a lower heat of vaporization and a lower specific heat than the conventional selective solvents of comparable C$_4$- or C$_5$-hydrocarbon selectivity. The lower viscosity of the solvent mixture to be used according to the invention results in a higher tray efficiency in the extractive distillation column, whilst as a result of the lower heat of vaporization and lower specific heat, energy can additionally be saved.

A further advantage of using a mixture of one of the relatively high-boiling selective solvents according to section (a) above with one of the relatively low-boiling organic solvents according to section (b) above is that the solvent recovery zone of the extraction unit for isolating the conjugated diolefin, which recovery zone is, for example, operated as a degassing zone or solvent stripping zone, can, for a given bottom temperature, be operated under higher pressure than is the case when using only the solvents according to (a) in accordance with conventional processes. This has the advantage, for example, that because of the higher pressure the degassed hydrocarbons obtained in the solvent recovery zone can in a simple manner, and without interpolation of a compressor or blower, be fed into downstream zones operated under higher pressure. Another advantage of using a mixture of one of the relatively high-boiling solvents according to (a) above with one of the lower-boiling solvents according to (b) above is that the solvent recovery zone of the extraction unit, which zone is, for example, operated as a degassing zone or solvent stripping zone, can, when using the same pressure as in conventional processes, be operated at a lower bottom temperature, so that contamination of the extraction unit by polymer formation can more easily be avoided.

It was surprising that the solvent mixture to be used according to the invention, for example a mixture of N-methylpyrrolidone and acetonitrile, exhibits as good a hydrocarbon selectivity as, for example, the mixture of N-methylpyrrolidone and water used in the prior art, since it is known that if acetonitrile is used as a selective solvent for isolating conjugated diolefins, the solvent only exhibits adequate hydrocarbon selectivity after addition of water (cf., for example, U.S. Pat. No. 3,317,627).

The process according to the invention employs a solvent mixture which comprises
  (a) from 50 to 99 percent by weight of a selective solvent boiling at from 140° to 260° C., preferably from 150° to 210° C. under atmospheric pressure, and
  (b) from 1 to 50 percent by weight of an organic solvent boiling at from 45° to 125° C., preferably from 50° to 115° C., especially from 55° to 105° C., under atmospheric pressure.

Examples of suitable selective solvents according to section (a) above are butyrolactone, furfuraldehyde, methoxypropionitrile and, preferably, N-alkyl-substituted lower aliphatic acid amides, eg. dimethylformamide, diethylformamide, dimethylacetamide, diethylacetamide and formylmorpholine, and N-alkyl-substituted cyclic aliphatic acid amides (lactams) having 5 ring members, eg. N-alkylpyrrolidones, where alkyl is of 1 to 3 carbon atoms, especially N-methylpyrrolidone. It is particularly advantageous to use dimethylformamide and especially N-methylpyrrolidone as the solvent (a).

Examples of suitable organic solvents according to section (b) above are nitriles, aliphatic and alicyclic ethers, lower aliphatic carboxylic acid esters and carbonic acid esters, amines, alcohols, aliphatic ketones, ether-amines, aliphatic hydrocarbons and aromatic hydrocarbons boiling at from 45° C. to 125° C. Examples of suitable nitriles are butyronitrile, propionitrile and, preferably, acetonitrile. Examples of suitable aliphatic ethers are symmetrical and unsymmetrical ethers of the general formula R—O—R', where, in general, the aliphatic radical R is a hydrocarbon radical of 1 to 5, preferably 1 to 4, carbon atoms, and the aliphatic radical R' is a hydrocarbon radical of 2 to 5, preferably 2 to 4, carbon atoms. The total number of carbon atoms of the two hydrocarbon radicals together is advantageously from 5 to 10, preferably from 5 to 9. Examples of suitable radicals R and R' are the ethyl, n-propyl, isopropyl, n-butyl, isobutyl and tert.-butyl radical and the amyl radicals, eg. tert.-amyl, and R may also be methyl. Examples of suitable ethers are symmetrical ethers, e.g. di-n-propyl ether, diisopropyl ether and diisobutyl ether, and, preferably, unsymmetrical ethers, e.g. methyl n-butyl ether, methyl tert.-butyl ether, ethyl tert.-butyl ether, n-propyl tert.-butyl ether, isopropyl tert.-butyl ether, isobutyl tert.-butyl ether, n-butyl tert.-butyl ether, methyl tert.-amyl ether, ethyl tert.-amyl ether, n-propyl tert.-amyl ether, ethyl isopropyl ether, n-propyl isopropyl ether, n-butyl isopropyl ether, isobutyl isopropyl ether and ethyl n-butyl ether. Particularly advantageous unsymmetrical ethers to use are those where one radical is tert.-amyl or especially tert.-butyl. Other examples of suitable aliphatic ethers are ethylene glycol monomethyl ether and preferably the dialkyl ethers of ethylene glycol and 1,2-propylene glycol, eg. ethylene glycol dimethyl ether, diethyl ether, methyl ethyl ether, methyl isopropyl ether and 1,2-propylene glycol dimethyl ether. Examples of suitable alicyclic ethers, ie. cyclic ethers which contain no hetero-atoms other than oxygen atoms, are 2-methyltetrahydrofuran, 3-methyltetrahydrofuran, 1,4-dioxane, tetrahydropyran and preferably tetrahydrofuran. Examples of suitable lower aliphatic carboxylic acid esters are those derived from lower monocarboxylic acids of, in general, 1 to 4, preferably 1 to 3, carbon atoms, such as formic acid, acetic acid and propionic acid. The alcohol component is in general derived from monohydric alcohols, advantageously of 1 to 5, preferably of 1 to 4, carbon atoms, eg. methanol, ethanol, propanol, isopropanol, n-butanol and isobutanol. Examples of suitable lower aliphatic carboxylic acid esters are formic acid esters, eg. ethyl formate, propyl formate, isopropyl formate, butyl formate and isobutyl formate; acetic acid esters, eg. methyl acetate and, preferably, ethyl acetate; and propionic acid esters, eg. methyl propionate and ethyl propionate. Examples of suitable carbonic acid esters are methyl ethyl carbonate and, preferably, dimethyl carbonate. Examples of suitable amines are primary aliphatic amines containing aliphatic hydrocarbon radicals of 4 or 5 carbon atoms, eg. n-butylamine, sec.-butylamine, isobutylamine, n-amylamine, isoamylamine, tert.-amylamine and sec.-n-amylamine; secondary aliphatic amines containing aliphatic hydrocarbon radicals of a total of 4 to 6 carbon atoms, eg. diethylamine, dipropylamine, diisopropylamine and piperidine; and tertiary aliphatic amines containing aliphatic hydrocarbon radicals of a total of 5 or 6 carbon atoms, eg. N,N-dimethylisobutylamine and triethylamine. Examples of suitable alcohols are those of 1 to 5 carbon atoms, eg. methanol, ethanol, propanol, isopropanol, butanol, isobutanol and tert.-amyl alcohol, isopropanol being preferred. Examples of suitable ketones are aliphatic ketones of a total of 3 to 5 carbon atoms, eg. acetone, methyl ethyl ketone, diethyl ketone and methyl propyl ketone. Examples of suitable ether-amines are alkoxyalkylamines of a total of 3 or 4 carbon atoms, eg. 2-methoxyethylamine, 2-ethoxyethylamine and 3-methoxypropylamine. Preferred aliphatic hydrocarbons are those of 6 to 8 carbon atoms, eg. hexanes, heptanes and octanes. Examples of suitable cycloaliphatic hydrocarbons are those of 6 to 8, preferably 6 or 7, carbon atoms, eg. cyclohexane and methylcyclohexane. Examples of suitable aromatic hydrocarbons are benzene and toluene. Amongst the solvents according to section (b) above, the use of the esters and preferably the nitriles, and especially the aliphatic or alicyclic ethers, is particularly advantageous.

The solvent mixture to be used according to the invention contains from 1 to 50 percent by weight, preferably from 2 to 25 percent by weight, especially from 3 to 20 percent by weight, of one of the organic solvents according to section (b) above. Correspondingly, it in general contains from 50 to 99 percent by weight, preferably from 75 to 98 percent by weight, especially from 80 to 97 percent by weight, of one of the solvents according to section (a) above. It is particularly advantageous to use a solvent mixture according to the invention which contains from 6 to 15 percent by weight of one of the organic solvents according to section (b) above.

The solvent mixture to be used according to the invention can contain a small amount of water, for example up to 10 percent by weight. Advantageously, however, the water content is restricted to at most 5 percent by weight, preferably at most 3 percent by weight, based on the solvent mixture. However, it can be advantageous to employ a substantially anhydrous solvent mixture, ie. a mixture containing at most 1 percent by weight, preferably at most 0.5 percent by weight, in particular at most 0.1 percent by weight, of water, based on the solvent mixture. If an organic solvent according to section (b) above is used which, as for example in the case of acetonitrile, forms an azeotropic mixture with water, it can furthermore be advantageous to employ a solvent mixture according to the invention which has a water content which roughly corresponds to the azeotropic ratio of water to organic solvent, based on the organic solvent contained in the solvent mixture. If water is added to a solvent mixture according to the invention in which acetonitrile is used as the organic solvent (b), the weight ratio of water to acetonitrile in the solvent mixture is advantageously from 1:3 to 1:9, preferably from 1:4 to 1:8.

The isolation of a conjugated diolefin from a $C_4$- or $C_5$-hydrocarbon mixture containing the latter, using the solvent mixture which according to the invention is to be employed as the selective solvent, is carried out in a conventional manner (cf., for example, German Pat. No. 1,184,334 and German Published Application DAS Nos. 1,568,876 and 1,568,902) by single-stage or multi-stage, advantageously single-stage or two-stage, extractive distillation. For example, the conjugated diolefins, eg. 1,3-butadiene, isoprene and 1,3-pentadiene, are isolated from the $C_4$- or $C_5$-hydrocarbon mixture by subjecting the latter, which contains both hydrocarbons which are more soluble and hydrocarbons which are less soluble than the conjugated diolefin, to an extractive distillation with the solvent mixture to be used according to the invention, from which distillation a distillate containing the less soluble hydrocarbons and an extract containing the conjugated diolefin, the more soluble hydrocarbons and the selective solvent are obtained. The conjugated diolefin can be isolated, from the extract, in the form of a crude product which is of adequate purity for certain applications, but which can also be subjected to additional purification operations, for example fractional distillation. Advantageously, however, the conjugated diolefin is isolated by using two successive extractive distillation stages using the solvent mixture to be employed according to the invention.

Using the latter method, the first stage of the extractive distillation results, for example, as already described above, in a distillate containing the less soluble hydrocarbons and an extract containing the conjugated diolefin, the more soluble hydrocarbons and the selective solvent. This extract is freed from the selective solvent, giving a mixture of the conjugated diolefin and the more soluble hydrocarbons. This mixture is subjected to a second extractive distillation using the selective solvent, giving the conjugated diolefin as the distillate, and an extract which contains the more soluble hydrocarbons and the selective solvent. The extract obtained is subsequently freed from the selective solvent, giving a hydrocarbon stream containing the more soluble hydrocarbons.

The hydrocarbon mixture, containing conjugated diolefins, used as the starting mixture for the process of the present invention may be a $C_4$- or $C_5$-fraction which was obtained by thermal cracking of a petroleum fraction (for example LPG, naphtha and the like), a butadiene-containing fraction obtained by dehydrogenation of n-butane and/or n-butene, or an isoprene-containing fraction obtained by dehydrogenation of isopentene and/or isoamylene. In general, the $C_4$-hydrocarbon mixture contains 1,3-butadiene as the conjugated diolefin, together with butanes, n-butene, isobutene, vinylacetylene, ethylacetylene and 1,2-butadiene, with or without small amounts of $C_3$- and/or $C_5$-hydrocarbons. The $C_5$-hydrocarbon mixture as a rule contains isoprene, trans- and cis-1,3-pentadiene and cyclopentadiene as conjugated diolefins, together with pentanes, n-pentenes, isoamylene, cyclopentene and higher acetylenes.

By way of example, extractive distillation of a $C_4$-fraction first gives a distillate containing the butanes and butenes, and an extract containing 1,3-butadiene, ethylacetylene, vinylacetylene and 1,2-butadiene, which extract, when subjected to a further extractive distillation, gives 1,3-butadiene as the distillate, whilst the extract contains ethylacetylene, vinylacetylene and 1,2-butadiene. The ethylacetylene, vinylacetylene and 1,2-butadiene are separated from the extract, containing these hydrocarbons, in a degassing unit, and the degassed solvent is recycled to the extractive distillation. The 1,3-butadiene obtained as the distillate can subsequently be subjected to a fractional distillation to remove the very small amounts of $C_3$- and/or $C_5$-hydrocarbons which may still be present.

The Examples which follow illustrate the invention.

EXAMPLE 1

A $C_4$ hydrocarbon mixture ($C_4$ fraction from an ethylene unit) having the composition shown in Table 1 is separated in a butadiene recovery unit having two extractive distillation zones arranged in series, a distillate containing the butanes and butenes and an extract containing 1,3-butadiene, ethylacetylene, vinylacetylene and 1,2-butadiene being obtained in the first extractive distillation zone. The extract is subjected to a second extractive distillation which gives 1,3-butadiene as a distillate, whilst the extract contains ethylacetylene, vinylacetylene and 1,2-butadiene. To remove the hydrocarbons by degassing, the extract is fed to a degassing unit in which the degassed selective solvent is obtained as the bottom product and a hydrocarbon stream containing vinylacetylene, ethylacetylene and 1,2-butadiene is obtained as the top product, which is, for example, fed as a waste stream to a power station, where it is burned.

TABLE 1

| Composition | % by weight |
|---|---|
| Propane | 0.03 |
| Propene | 0.10 |
| Propadiene | 0.02 |
| Propyne | 0.15 |
| n-Butane | 3.1 |
| i-Butane | 1.0 |
| But-1-ene | 14.0 |
| i-Butene | 27.0 |
| Trans-but-2-ene | 5.0 |
| Cis-but-2-ene | 4.3 |
| 1,3-Butadiene | 44.0 |
| 1,2-Butadiene | 0.2 |
| Ethylacetylene | 0.2 |
| Vinylacetylene | 0.7 |
| $C_5$-hydrocarbons | 0.2 |

The selective solvent used is a mixture of 88% by weight of N-methylpyrrolidone (NMP), 10% by weight of acetonitrile (ACN) and 2% by weight of water (the mixture constituting a solvent according to the invention), in which the contents of ACN and water correspond to the azeotropic ACN/water mixture under 1 bar.

In a Comparative Experiment, a prior art mixture of 91.7% by weight of NMP and 8.3% by weight of water (comparative solvent) is used in place of the solvent according to the invention.

The hydrocarbon selectivities (taking 1,3-butadiene as 1) found for the solvent according to the invention and for the comparative solvent are shoen in Table 2:

TABLE 2

| | i-Butene | But-2-ene trans | But-2-ene cis | 1,3-Butadiene | Ethylacetylene |
|---|---|---|---|---|---|
| 91.7% by weight of NMP/ 8.3% by weight of $H_2O$ | 2.63 | 2.17 | 1.85 | 1 | 0.36 |
| 88% by weight of NMP/ 10% by weight of ACN/ 2% by weight of $H_2O$ | 2.58 | 2.20 | 1.82 | 1 | 0.36 |

The selectivities in respect of the key component of the first extractive distillation (cis-but-2-ene) and the key component of the second extractive distillation (ethylacetylene) are identical, within the accuracy of measurement, for the comparative solvent and for the solvent according to the invention. (The selectivity is the ratio of the Bunsen absorption coefficients of 1,3-butadiene and of the hydrocarbon to be separated off).

Under 4.5 bar, the solvent according to the invention exhibits a solubility toward the $C_4$-hydrocarbon mixture which is about 60% higher than that of the comparative solvent. Hence, when using the solvent according to the invention instead of the comparative solvent, the amount of selective solvent to be provided for the first and second extractive distillations can accordingly be reduced by about 60%. This reduces the column diameters of the extractive distillation columns by about 30%. Since the heights of the extractive distillation columns can furthermore be reduced by about 25% because of the increased tray efficiency—described below—when using the solvent according to the invention, the cost of the equipment required for the extractive distillation columns can be reduced by more than 50% when using the solvent according to the invention.

At the same time, as a result of the reduced amount of selective solvent to be fed to the extractive distillations when using the solvent according to the invention, the steam consumption can be reduced by about 10%.

Using the solvent according to the invention, the trays of the extractive distillation columns have an efficiency which is 27% higher than when using the comparative solvent. As a result, when using the solvent according to the invention, extractive distillation columns reduced in height by about 25% compared to those employed with the comparative solvent can be used to achieve the same degree of separation.

In the temperature range of from 130° to 160° C., which is the important range for degassing, the vapor pressures of the solvent according to the invention and of the comparative solvent are virtually identical. For example, at 150° C., degassing of the extract obtained after the second extractive distillation gives a pressure in the degasser of about 1.7 bar, which is sufficiently high to be able to feed the off-gas mixture, containing the $C_4$-acetylenes (vinylacetylene and ethylacetylene) directly, without interpolation of a compressor or blower, to a power station or to a waste gas flare operating under atmospheric pressure. Hence, if the gas is to be burned in a flare, it is not necessary to employ a special low-pressure flare.

EXAMPLE 2

This Example illustrates the single-stage extractive distillation of a $C_4$-hydrocarbon mixture.

0.716 kg/h of a $C_4$-hydrocarbon mixture of the following composition is fed to the bottom of a packed column, of 25 mm internal diameter and 2.50 m height, operated under 1 bar at 15° C.:

| Composition | % by weight |
|---|---|
| i-Butane | 1.33 |
| n-Butane | 4.44 |
| But-1-ene | 11.65 |
| i-Butene | 28.21 |
| Trans-but-2-ene | 7.28 |
| Cis-but-2-ene | 4.45 |
| 1,3-Butadiene | 41.98 |
| 1,2-Butadiene | 0.31 |
| Ethylacetylene | 0.24 |
| Vinylacetylene | 0.11 |

At the top of the column, 4.62 kg/h of recycled selective solvent containing 88 percent by weight of N-methylpyrrolidone, 10 percent by weight of acetonitrile and 2 percent by weight of water are introduced at 15° C. 0.374 kg/h of raffinate containing 7.46 percent by weight of 1,3-butadiene and 5.61 percent by weight of cis-but-2-ene (key component for the separation) are taken off as gas at the top of the column. 1,2-Butadiene and the $C_4$-acetylenes (ethylacetylene and vinylacetylene) are no longer detectable in the raffinate. At the bottom of the column, an extract containing the more readily soluble hydrocarbons is taken off and is then degassed by feeding it to the top of a downstream column which has 10 bubble-cap trays and is operated at a bottom temperature of 130°–140° C. From the bottom of this column, the selective solvent which has been substantially freed from the hydrocarbons is recycled, after cooling, to the top of the packed column. At the center of the bubble-cap tray column, 0.342 kg/h of crude butadiene containing 79.80 percent by weight of 1,3-butadiene are taken off. The hydrocarbons issuing at the top of the bubble-cap tray column are recycled, as gas, to the bottom of the packed column.

COMPARATIVE EXPERIMENT

In a comparative experiment, the procedure described in Example 2 above is followed, except that the selective solvent used is a mixture of 91.7 percent by weight of N-methylpyrrolidone and 8.3 percent by weight of water, which is fed to the packed column in a larger amount than in Example 2, namely 6.00 kg/h, and that the $C_4$-hydrocarbon mixture is introduced at the bottom of the packed column in a lower amount than in Example 2, namely 0.471 kg/h, 0.235 kg/h of raffinate and 0.236 kg/h of crude butadiene being obtained. Though in the Comparative Experiment the ratio of the feed of selective solvent to the feed of $C_4$-hydrocarbon mixture (12.74) is virtually doubled compared to the corresponding ratio in Example 2 (6.45), the Comparative Experiment, in which the ratio of the amount of raffinate and the amount of crude butadiene (0.235/0.236) is virtually the same as inby weight of 1,3-butadiene. Furthermore, the key component cis-but-2-ene is concentrated to a lesser degree in the raffinate from the Comparative Experiment (4.41% by weight of cis-but-2-ene) than in the raffinate according to Example 2 (5.61 percent by weight of the cis-but-2-ene). Whilst 1,2-butadiene, ethylacetylene and vinylacetylene are present in the raffinate from the Comparative Experiment in an amount which is still clearly detectable, the contents of these components in the raffinate according to Example 2 are below the limit of detectability. Furthermore, the crude butadiene obtained in the Comparative Experiment contains only 69.07 percent by weight of 1,3-butadiene, whilst the crude butadiene according to Example 2 contains 79.80 percent by weight.

EXAMPLE 3

The procedure followed is as described in Example 2, except that 0.858 kg/h of $C_4$-hydrocarbon mixture are fed to the bottom of the packed column and 4.60 kg/h of recycled selective solvent, comprising 90 percent by weight of N-methylpyrrolidone and 10 percent by weight of methyl tert.-butyl ether, are fed to the top of this column. 0.418 kg/h of raffinate containing 7.89 percent by weight of 1,3-butadiene and 4.78 percent by weight of cis-but-2-ene are taken off as a gas at the top of the column. At the center of the bubble-cap tray column, 0.440 kg/h of crude butadiene containing 74.55 percent by weight of 1,3-butadiene are taken off.

COMPARATIVE EXPERIMENT

In a Comparative Experiment, the procedure described in Example 3 above is followed, except that the selective solvent used is a mixture of 91.7 percent by weight of N-methylpyrrolidone and 8.3 percent by weight of water, which is fed to the packed column in a larger amount than in Example 3, namely 6.00 kg/h, and that the $C_4$-hydrocarbon mixture is introduced at the bottom of the packed column in a lower amount than in Example 3, namely 0.471 kg/h, 0.235 kg/h of raffinate and 0.236 kg/h of crude butadiene being obtained. Though in the Comparative Experiment the ratio of the feed of selective solvent to the feed of $C_4$-hydrocarbon mixture (12.74) is increased by 138% compared to the corresponding ratio in Example 3 (5.36), the Comparative Experiment, in which the ratio of the amount of raffinate and the amount of crude butadiene (0.235/0.236) is virtually the same as in Example 3 (0.418/0.440), gives a raffinate containing 14.77 percent by weight of 1,3-butadiene, whilst the raffinate according to Example 3 only contains 7.89 percent by weight of 1,3-butadiene. Furthermore, the key component cis-but-2-ene is concentrated to a lesser degree in the raffinate from the Comparative Experiment (4.41 percent by weight of cis-but-2-ene) than in the raffinate according to Example 3 (4.78 percent by weight of cis-but-2-ene). Whilst 1,2-butadiene, ethylacetylene and vinylacetylene are present in the raffinate from the Comparative Experiment in an amount which is still clearly detectable, the contents of these components in the raffinate according to Example 3 are below the limit of detectability. Furthermore, the crude butadiene obtained in the Comparative Experiment contains only 69.07 percent by weight of 1,3-butadiene, whilst the crude butadiene according to Example 3 contains 74.55 percent by weight.

EXAMPLE 4

The procedure followed is as described in Example 2, except that 0.700 kg/h of $C_4$-hydrocarbon mixture are fed to the bottom of the packed column and 4.46 kg/h of recycled selective solvent, comprising 90 percent by weight of N-methylpyrrolidone and 10 percent by weight of toluene, are fed to the top of this column. 0.350 kg/h of raffinate containing 8.53 percent by weight of 1,3-butadiene and 4.45 percent by weight of cis-but-2-ene are taken off as a gas at the top of the column. At the center of the bubble-cap tray column, 0.350 kg/h of crude butadiene containing 75.42 percent by weight of 1,3-butadiene are taken off.

COMPARATIVE EXPERIMENT

In a Comparative Experiment, the procedure described in Example 4 above is followed, except that the selective solvent used is a mixture of 91.7 percent by weight of N-methylpyrrolidone and 8.3 percent by weight of water, which is fed to the packed column in a larger amount than in Example 4, namely 6.00 kg/h, and that the $C_4$-hydrocarbon mixture is introduced at the bottom of the packed column in a lower amount than in Example 4, namely 0.471 kg/h, 0.235 kg/h of raffinate and 0.236 kg/h of crude butadiene being obtained. Though in the Comparative Experiment the ratio of the feed of selective solvent to the feed of $C_4$-hydrocarbon mixture (12.74) is increased by 89% compared to the corresponding ratio in Example 4 (6.73), the Comparative Experiment, in which the ratio of the amount of raffinate and the amount of crude butadiene (0.235/0.236) is virtually the same as in Example 4 (0.350/0.350), gives a raffinate containing 14.77 percent by weight of 1,3-butadiene, whilst the raffinate according to Example 4 only contains 8.53 percent by weight of 1,3-butadiene. Whilst 1,2-butadiene, ethylacetylene and vinylacetylene are present in the raffinate from the Comparative Experiment in an amount which is still clearly detectable, the contents of these components in the raffinate according to Example 4 are below the limit of detectability. Furthermore, the crude butadiene obtained in the Comparative Experiment contains only 69.07 percent by weight of 1,3-butadiene, whilst the crude butadiene according to Example 4 contains 75.42 percent by weight.

EXAMPLE 5

In a single-stage extractive distillation of a $C_4$-hydrocarbon mixture, a packed column of 25 mm internal diameter and 2.50 m height, operated under 1 bar at 15° C., is fed, at the bottom, with 0.768 kg/h of a $C_4$-hydrocarbon mixture of the composition shown in Example 2. At the top of the column, 4.50 kg/h of recycled selective solvent, containing 90 percent by weight of dimethylformamide and 10 percent by weight of ethyl acetate, are introduced at 15° C. 0.379 kg/h of raffinate are taken off as gas at the top of the column. At the bottom of the column, an extract containing the more readily soluble hydrocarbons is obtained, and this is degassed by feeding it to the top of a downstream column which has 10 bubble-cap trays and is operated at a bottom temperature of about 140° C. From the bottom of this column, the selective solvent, which has been substantially freed from the hydrocarbons, is recycled, after cooling, to the top of the packed column. At the center of the bubble-cap tray column, 0.389 kg/h of crude butadiene containing 80.61 percent by weight of 1,3-butadiene are taken off. The hydrocarbons issuing at the top of the bubble-cap tray column are recycled, as gas, to the bottom of the packed column. The ratio S/M of the circulating solvent S (4.60 kg/h) to the $C_4$-hydrocarbon mixture feed M (0.768 kg/h) is 5.99.

COMPARATIVE EXPERIMENT

In a Comparative Experiment, the procedure described in Example 5 above is followed except that pure dimethylformamide is used as the selective solvent and the $C_4$-hydrocarbon mixture is introduced into the bottom of the packed column in a lower amount than in Example 5, namely at the rate of 0.621 kg/h; 0.306 kg/h of raffinated and 0.315 kg/h of crude butadiene are obtained, ie. the $C_4$-hydrocarbon mixture is divided into raffinate and crude butadiene in virtually the same ratio as in Example 5. The key components cis-but-2-ene and 1,3-butadiene have the same contents in the raffinate and crude butadiene in the Comparative Experiment as in Example 5. The S/M ratio of circulation solvent S (4.60 kg/h) to feed M of $C_4$-hydrocarbon mixture (0.621 kg/h) is 7.41, ie. in the Comparative Experiment the S/M ratio had to be about 23% higher than in Example 5 in order to achieve the same degree of success of the separation.

EXAMPLE 6

The procedure described in Example 2 and the corresponding Comparative Experiment is followed, except that in Example 6 the selective solvent is a mixture of 90 percent by weight of N-methylpyrrolidone and 10 percent by weight of tetrahydrofuran and the S/M ratio of circulating solvent S to feed M of C$_4$-hydrocarbon mixture is maintained at 6.50, whilst in the Comparative Experiment accompanying Example 6 an S/M ratio of 12.74 is maintained to achieve the same degree of success of the separation, ie. in the Comparative Experiment the S/M ratio had to be 96% higher than in the Example in order to achieve the same degree of success of the separation.

EXAMPLE 7

The procedure described in Example 5 and the corresponding Comparative Experiment is followed, except that in Example 7 the temperature is 5° C. higher, the selective solvent is a mixture of 90% by weight of N-methylpyrrolidone and 10% by weight of diethyl carbonate and the S/M ratio of circulating solvent S to feed M of C$_4$-hydrocarbon mixture is maintained at 6.60, whilst in the Comparative Example accompanying Example 7, the selective solvent is a mixture of 91.7% by weight of N-methylpyrrolidone and 8.3% by weight of water and an S/M ratio of circulating solvent S to feed of C$_4$-hydrocarbon mixture of 12.74 is maintained.

This means that to achieve the same degree of success of the separation in the Comparative Experiment accompanying Example 7 as in Example 7 itself, the S/M ratio had to be 93% higher.

We claim:

1. A process for isolating a conjugated diolefin from a C$_4$- or C$_5$-hydrocarbon mixture containing the diolefin by extractive distillation using a selective solvent, wherein the selective solvent is a solvent mixture which comprises
    (a) from 80 to 97 percent by weight of dimethylformamide, diethylformamide, dimethylacetamide, diethylacetamide, formylmorpholine, N-methylpyrrolidone, butyrolacetone or methoxypropionitrile and
    (b) from 3 to 20 percent by weight of acetonitrile, said solvent mixture containing at most 5 percent by weight of water, based on the solvent mixture.
2. The process of claim 1, wherein butadiene is isolated from a C$_4$-hydrocarbon mixture containing butadiene.

* * * * *